United States Patent [19]

Weithmann

[11] Patent Number: 5,043,328

[45] Date of Patent: Aug. 27, 1991

[54] FORMULATIONS CONTAINING UNSATURATED FATTY ACIDS FOR THE SYNTHESIS OF PROSTAGLANDINS AND HYDROXY-FATTY ACIDS IN BIOLOGICAL SYSTEMS

[75] Inventor: Klaus U. Weithmann, Hofheim am Taunus, Fed. Rep. of Germany

[73] Assignee: Hoechst Aktiengesellschaft, Frankfurt am Main, Fed. Rep. of Germany

[21] Appl. No.: 304,717

[22] Filed: Feb. 1, 1989

Related U.S. Application Data

[62] Division of Ser. No. 46,650, May 7, 1987, abandoned.

[30] Foreign Application Priority Data

May 9, 1986 [DE] Fed. Rep. of Germany ....... 3615710

[51] Int. Cl.$^5$ .... A61K 31/685; A61K 31/385/31/355; A61K 31/20
[52] U.S. Cl. .................................. 514/78; 514/440; 514/458; 514/560; 514/768; 514/973
[58] Field of Search ............... 514/768, 560, 440, 458, 514/973, 78

[56] References Cited

U.S. PATENT DOCUMENTS

| 4,668,704 | 5/1987 | Hollander et al. | 514/560 |
| 4,780,456 | 10/1988 | Pistolesi | 514/560 |
| 4,874,603 | 10/1989 | Fratzer | 514/560 |

FOREIGN PATENT DOCUMENTS

| 2425988 | 5/1974 | Fed. Rep. of Germany | 514/560 |
| 184011 | 9/1985 | Japan | 514/440 |
| 187425 | 8/1987 | Japan | 514/560 |

*Primary Examiner*—Frederick E. Waddell
*Assistant Examiner*—Kevin Weddington
*Attorney, Agent, or Firm*—Finnegan, Henderson, Farabow, Garrett, and Dunner

[57] ABSTRACT

The present invention relates to formulations containing unsaturated fatty acids for the synthesis of prostaglandins and hydroxy-fatty acids in biological systems and to the use of such formulations for the preparation of medicaments which are suitable for curing prostaglandin deficiencies in humans or animal, for example healing or preventing diseases of the gastro-intestinal tract.

16 Claims, No Drawings

FORMULATIONS CONTAINING UNSATURATED FATTY ACIDS FOR THE SYNTHESIS OF PROSTAGLANDINS AND HYDROXY-FATTY ACIDS IN BIOLOGICAL SYSTEMS

This is a division of application Ser. No. 07/046,650, filed May 7, 1987, now abandoned.

Long-chain polyunsaturated fatty acids or their esters and other derivatives are of importance as a starting material for the enzyme-catalyzed preparation of prostaglandins and hydroxy-fatty acids. Thus, for example by means of cells or of cell homogenates or cell fractions, the products, which can otherwise be prepared only by involved chemical processes, can be obtained preparatively by a biochemical method especially from dihomo-gamma-linolenic acid, arachidonic acid or eicosapentaenoic acid as the substrates. In such preparative problems, the aim will be a stimulation of the formation of the desired prostaglandin. This can be achieved by addition of suitable enzyme co-factors. However, the said fatty acids can also be used for medical purposes, for example in clinical investigations of the ability of body cells, or cell homogenates or cell fractions (for example keratinocytes; blood vessel cells obtained by biopsy; cells or homogenates of the medulla of kidney), to metabolize the particular fatty acid or to convert it to prostaglandins having a certain biological action. In such medical problems, it is not important whether the prostaglandin formed is homogeneous, but there will be an aim of stimulating the formation of the prostaglandin serving as the medical parameter to be measured.

The present invention describes novel, stable formulations which contain long-chain polyunsaturated fatty acids, by means of which preparations prostaglandins and hydroxy-fatty acids which can be used for the said purposes can advantageously be prepared.

It is already known that the conversion of polyunsaturated fatty acids, such as arachidonic acid, can be stimulated by prostaglandin-synthesizing enzymes with the aid of certain co-factors and, thus, the synthesis of very particular prostaglandins can also be promoted. For example, in biochemical pharmacology 31(1982), 3591, an in vitro system is described which converts arachidonic acid by means of the enzyme obtained from seminal vesicles of sheep, in each case with or without addition of the co-factors glutathione and hydroquinone. In loc. cit., page 3595, it is explained that the conversion is accelerated by the said co-factors. A similar system of arachidonic acid, homogenate of rabbit kidney medulla, glutathione and hydroquinone is described in Life Sciences 26 (1980) 765.

For the purposes mentioned above, aqueous reagent formulations have now been prepared, which contain the polyunsaturated fatty acids preferably in combination with stimulating enzyme co-factors. Such formulations are not only novel but also show unexpected properties. As explained in detail below, these stimulators without exception modify the stability of the fatty acids in a surprising manner. Thus, within a short time, a markedly greater quantity of undesired decomposition and conversion products of arachidonic acid can form in arachidonic acid formulations containing glutathione or hydroquinone, than is the case in formulations which do not contain these additions. These byproducts are highly reactive and can trigger undesired, even biological side reactions. Our own investigations described in more detail below, however, show that the prostaglandin synthesis can also be stimulated by mixtures which contain polyunsaturated fatty acids, such as arachidonic acid, together with other sulfur-containing compounds such as the disulfide lipoic acid or the reduced thiols homocysteine and cysteine or their derivatives acylated on the nitrogen atom, much smaller quantities of undesired byproducts being formed according to the invention. This is surprising, since it was not possible to achieve these advantageous effects with other sulfur compounds occurring in nature or derived from natural compounds, such as co-enzyme A or its scission or hydrolysis products cysteamine and pantetheine, or dihydrolipoic acid, cystine and mono- or poly-thiol sugar compounds such as dithiothreitol or dithioerythritol. In the experimental part, it is stated that the undesired side reactions can be fully suppressed by an addition of lipoic acid, but can be largely, but not completely suppressed by an addition of the other sulfur-containing compounds according to the invention.

In fact, it is already known that the conversion of arachidonic acid or the synthesis of certain prostaglandins can also be stimulated by an addition of substances without a sulfur content, for example, as cited above, by means of hydroquinone and also phenol, adrenalin, noradrenalin, tryptophan, 5-hydroxytryptophan and ascorbic acid. Surprisingly, it has now been found that the undesired decomposition of polyunsaturated fatty acids, for example of arachidonic acid, in an aqueous medium is considerably accelerated by these stimulators. The use of, for example, 2-butanol or pyridine instead of water has an additional destabilizing effect, whereas the undesired byproducts surprisingly do not arise when dimethyl sulfoxide or ethanol or polyols such as glycerol or polyethylene glycol are used. Organic solvents have, however, the disadvantage that they denature enzymes; they must therefore be removed before the enzyme reaction or diluted with water. The residues which remain after the removal of the solvent and which consist of an intimate mixture of unsaturated fatty acid and stimulator are, surprisingly, again unstable. It has not yet been described that surprisingly advantageous aqueous formulations for the stimulation of the prostaglandin synthesis can be obtained with tyrosine. As explained in the experimental part, formulations which contain unsaturated fatty acids and tyrosine or tyrosine-like compounds are, surprisingly, completely stable.

However, even aqueous mixtures or solutions of unsaturated fatty acid and the other abovementioned stimulators can be fully stabilized, namely by an addition of lipids which are soluble or emulsifiable in water, or of proteins which can be prepared, for example, from human or mammal blood, such as serum albumin or globulins, such as gamma-globulin, or porphyrin-containing proteins such as hemoglobin, methemoglobin or cytochromes. Vitamins of the E series and flavonoids, in particular those with a sugar moiety, for example rutin or troxerutin (for the nomenclature, see "The Merck Index", 10th edition, 1983, Rahway, N.J., U.S.A.) are also suitable according to the invention, whereas sugars without a flavone moiety, such as rhamnoglucose, glucose and sorbitol, are not stabilizing. Surprisingly, however, the formulations according to the invention can be prepared with the aid of cyclodextrins.

With respect to stabilization with serum albumins, it is indeed known per se that albumins can bond long-chain fatty acids at an energetically low level, but it is the more surprising that the fatty acids bonded in this way behave like freely dissolved fatty acids in the reagent formulations according to the invention, that is to say they are enzymatically converted without hindrance. It has also already been described (cf., for example, Journal of Biological Chemistry 253 (1978) 5061) that the enzymes of the prostaglandin synthesis contain heme or other porphyrins bonded as prosthetic groups. However, this requires only extremely small quantities of porphyrin-containing enzymes, which do not have any stabilizing effect on the added quantities of unsaturated fatty acid. There is no indication to be found in the literature to the effect that a stabilizing reagent for stimulating the enzyme-catalyzed prostaglandin synthesis can be prepared with a higher proportion of porphyrin-containing proteins.

Stable formulations which contain fatty acids having 20 to 22 carbon atoms and 3 or more double bonds in each case and, as stabilizers, a proportion of up to 30 percent by weight of phospholipids, for example lecithin, have been disclosed in DE 34,197,996 A1. Such stable formulations can likewise be used according to the invention in combination with the stimulators already mentioned.

As explained in the experimental part, however, it is more appropriate to add more than 30 percent by weight of phospholipid, for example lecithin, to the formulations of the unsaturated fatty acids having 18 to 22 carbon atoms, because more stable mixtures are then obtained. A formulation which contains up to 90% by weight of phospholipid, preferably 50 to 80 percent by weight of phospholipid, is advantageous. With a view to medical activities, a formulation is preferred which contains fatty acids, according to the invention having 18 carbon atoms. A formulation containing unsaturated fatty acids and a proportion of phospholipids greater than 30 percent by weight has already been proposed as a dietary product (EP 0,148,303 A1). Stabilizing effects of the phospholipids on the unsaturated fatty acids are not disclosed in EP 0,148,303 A1. Neither is there any indication of the formulations, claimed in the present application and composed of unsaturated fatty acids, phospholipids and stimulators, being advantageously suitable for the uses claimed in the present application, especially for the claimed medical applications.

The invention therefore relates to solid or liquid mixtures of substances or solutions, which comprise A) one or more unsaturated fatty acid(s), defined by three to five isolated double bonds and 18 to 22 carbon atoms which are arranged in a straight chain and can be methylated or ethylated at one or two carbon atoms in positions 2, 3, 4, 16, 17, 18, 19 or 20, as the free carboxylic acid with terminal-$CO_2H$ or as the carboxamide or as —$CO_2X$, X being a protective group which can be eliminated under acidic conditions, such as an alkyl radical, for example an ethyl or propyl radical, or a 1- or 2-lysophospholipid, for example 2-lysolecithin, or a metal or amine cation or the cationic form of an ion exchanger, B) as stimulators with, in some cases, a simultaneous stabilizing action, one or more compounds from the following groups:
B₁) a phenolic compound of the formula I

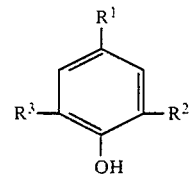

in which the radicals $R^2$ and $R^3$ are hydroxyl groups or hydrogen and $R^1$ is a radical —OH, —$CO_2H$, —$CH_2$—$CO_2$—H, —CH=CH—$CO_2H$, —$CH_2$—$CHR^4R^5$ or —CHOH—$CH_2$—NH—$R^6$ with $R^4$=—H or —$CO_2H$ and $R^5$=—H or —$NH_2$ and $R^6$=—H, —$CH_3$ or —$C_2H_5$, B₂) an indole derivative of the formula II

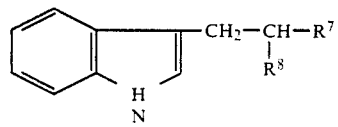

in which $R^7$ is hydrogen or —COOH, $R^8$ is hydrogen or —$NH_2$ and $R^9$ is nitrogen or —OH, B₃) is cysteine or homocysteine, or lipoic acid, the acylic alkyl radical of which can be shortened by up to four methylene groups, B₄) a peptide comprising a maximum of ten amino acids, wherein one or more of the amino acids are replaced by in each case one of the compounds according to B₁) to B₃), B₅) a compound according B₁) to B₄) which can carry a $C_1$-$C_4$-alkanoyl group on one N atom, B₆) a flavone derivative which is substituted by at least one hydroxyl group which can carry a sugar radical, B₇) a salt of the ionic forms of the compounds according to B₁)-B₆) and, if appropriate, B₈) a carboxylic acid compound according to B₁) to B₇) which can be esterified with an alkoxy radical or be in the form of a carboxamide which can also be mono- or di-alkylated, and, if appropriate C) as stabilizers, one or more compounds from the following groups:
C₁) dimethyl sulfoxide, ethyl alcohol, glycerol, ethylene glycol, polyethylene glycol or glycerol triacetate and
C₂) phospholipids, sugar lipids, cyclodextrins, proteins, for example those which can be prepared from human and mammal blood, or vitamins of the E series, as a stable formulation for the synthesis of prostaglandins and hydroxy-fatty acids in biological systems.

Examples of metal cations X which can be used are those of the alkali metals, such as lithium, sodium and potassium, and of the alkaline earth metals such as magnesium and calcium, and also cationic forms of other metals such as aluminum, zinc and iron, if appropriate in a form chelated with citric acid or ethylenediaminetetraacetic acid and the like. The amine cations can be those of primary, secondary or tertiary amines such as the alkylamines, for example mono-, di-, and trimethylamine or -ethylamine, -propylamine, -isopropylamine, -butylamine, -isobutylamine and -t-butylamine, and N-methyl-hexylamine, benzylamine, β-phenyl-ethylamine, ethylenediamine, di-ethylenetriamine, pyrrolidine, piperidine, morpholine, piperazine, mono-, di- and tri-ethanolamine, ethyldiethanolamine, N-butylethanolamine, tris-(hydroxymethyl)-aminomethane and the like. Examples of suitable amine salts are those of tryptamine and cysteine and the basic amine salts of lysine and arginine. Examples of suitable quaternary ammonium cations are tetramethyl ammonium, tetraethyl ammonium and benzyltrimethyl ammonium. These cations can also be used for forming salts of the anionic forms of the compounds according to $B_1$) to $B_6$), whereas chloride and fluoride are preferred for forming salts of the cationic forms.

The fatty acids preferred for the enzymatic reaction are those designated as 18:2 $\omega$-6, 20:4 $\omega$-6, 22:5 $\omega$-6, 18:3 $\omega$-3, 20:5 $\omega$-3, 22:6 $\omega$-3, 18:3 $\omega$-6, 20:3 $\omega$-6, 22:4 $\omega$-6 and 22:4 $\omega$-3, the first figure in the conventional nomenclature denoting the number of carbon atoms, the figure after the colon denoting the number of double bonds and the figure after the $\omega$ denoting the position of the first double bond counted from the methyl end of the molecule. The products from certain fatty acids are already known, and it is also known that the rate of reaction of the unsaturated fatty acids and the formation of defined products can be promoted by the use of certain stimulators. As is explained in more detail in the experimental part, the present invention makes it possible to stimulate the formation of defined fatty acid products in an advantageous manner. The selection of the composition of the formulation according to the invention with respect to the type of unsaturated fatty acid, type of stimulator and also type of stabilizer will therefore depend entirely on the particular problem.

Where the stimulators are amino acids or peptides, both the L- form and the D- form and also mixtures of the D- and L- forms can be used.

Stimulators of the formula I with $R^2=R^3=-H$ and $R^1=-CH_2-CH(NH_2)-CO_2H$, and peptides which contain these, or lipoic acid, the side chain of which can be shortened, or flavonoids have the particular advantage that they enhance the stability of the fatty acids even without an additional stabilizer.

The quantities of the unsaturated fatty acids to be used in the formulations according to the invention are also dependent on the desired application. For the preparative production of prostaglandins, any desired quantity of the formulation can be apportioned. For the preparation of reagent formulations according to the invention, which serve for use in clinical-chemical tasks, i.e. for example for investigating the ability of cells or cell constituents, such as blood cells or biopsy material from the kidney, lung, stomach and the like, to convert unsaturated fatty acids or to synthesize prostaglandins with a defined biological activity, reagent mixtures according to the invention suffice which contain 5 mg to 1 pg, preferably 100 $\mu$g to 1 ng, of unsaturated fatty acid. The reagents can be in the form of a suspension or solution, for example in water, ethanol, ethylene glycol, polyethylene glycols or glycerol or mixtures of these solvents. After the solvent has been removed, the reagents are in the form of mixtures or blends. Removal of the organic solvents is necessary in particular when the reagent mixtures are used for enzyme-catalyzed reactions in vitro.

Enzyme systems, obtainable from biological material, for the preparation of prostaglandins are known per se. It is also known that, depending on the origin and nature of the biological material, different prostaglandins can be synthesized. The reagents according to the invention can then be used for the preparation of these prostaglandins. For this purpose, a solution or suspension or homogenate of the biological material is mixed with the formulations according to the invention and incubated in the known manner. The synthesis of defined prostaglandins can be controlled to a certain extent by the selection of the stimulator. Undesired fatty acid products, such as thromboxan or leucotrienes, can be suppressed, according to the state of the art, by an addition of thromboxan inhibitors or lipoxygenase inhibitors. If the unsaturated fatty acid in the reagent is in a bonded form, for example as the ester, care must be taken to convert it into the free form before or during the enzymatic reaction, if appropriate by means of the lipase enzymes present anyway in biological material, or by an addition of suitable lipase enzymes or, even before the enzymatic reaction, by the known processes of chemical hydrolysis. After the extraction of the prostaglandin formed, or of the prostaglandins formed, by means of suitable extractants, for example ethyl acetate, the desired prostaglandin can be produced in the pure form, for example by means of known chromatographic methods, such as high-pressure liquid chromatography. The quantitative proportions of the constituents according to the invention in the formulations can vary within wide limits. They depend on the nature of the unsaturated fatty acid, on the stimulator used or on the stabilizer and also on the intended use. The weight ratio between unsaturated fatty acid (relative to the free acid) and stimulator is in general between 50 and 0.1, preferably between 20 and 0.5. The quantity of the added stabilizer is chosen such that its proportion by weight, relative to the free unsaturated fatty acid, is between about 0.5 and 100, preferably between 1 and 15 and especially between 2 and about 8 to 10.

Biological systems can also be treated in vivo with the medically suitable formulations according to the invention, and this is in fact more advantageous than is possible with the individual components of the formulations according to the invention. However, a systemic (for example intravenous) administration of the formulations according to the invention is inappropriate, because the unsaturated fatty acids can be metabolized before they reach the site of action. By contrast, for example the cells of the skin, mouth, oesophagus, nose, eyes, intestines and stomach and of the bronchial and lung tract are directly accessible.

Prostaglandin defiencies in humans or animals, for example in the gastro-intestinal tract, which lead to, for example, disturbances in gastric juice secretion and to gastro-intestinal lesions (ulcers), can be treated, for example, with formulations according to the invention in the form of oral (peroral) medicament forms. The intestines can also be treated with medicament forms which have been coated enterically (insoluble in gastric acid). If it is desired to induce diarrhea, for example in the case of constipation, medicament forms for rectal therapy can also be used, whereas intravaginal therapy can be used for inducing labor, for example for starting the birth process. Malfunctions of the skin and of the connective tissue region below the skin can be treated by dermal formulations according to the invention. Oral formulations and suppositories for human therapy are of such a composition that they contain, per dosage unit, between 0.5 and 2,000 mg, in general between 2 and 1,000 mg and preferably between 5 and 250 mg, of unsaturated fatty acid. In the case of illnesses resistant to therapy, for example obstinate constipation, it can also be appropriate to apply a dosage unit of up to 6,000 mg or more of unsaturated fatty acid. Suprisingly, the straight-chain fatty acids according to the invention having 18 carbon atoms and also those having 22 carbon atoms are equally effective as therapeutics for gastro-intestinal ulcers as the fatty acids containing 20 carbon atoms. This is of medical importance, because they cause fewer side effects such as diarrhea. A suitable therapy comprises, for example, the administration of one, two or more, preferably 3 to 8, individual dosages per day of the formulation according to the invention, the required quantity depending on the number of individual doses and also on the disease to be treated, and one dose can also be made up, for example, from several single doses administered simultaneously.

It is known that gastro-intestinal intolerances, which lead to gastro-intestinal ulcers, can arise as undesired side effects of certain medicaments. The formulations according to the invention are also suitable for the prevention or therapy of such damage to the gastro-intestinal mucosa. The treatment with the formulations can take place either before, or simultaneously with, or after the administration of the medicaments causing damage to the mucosa. It is particularly advantageous to combine the reagents according to the invention with the medicaments which are causing damage to the gastric mucosa, in a suitable pharmaceutical formulation. In this case, the components can either be compartmentalized or can be in the form of a mixture. Numerous medicaments which cause stomach intolerances or gastro-intestinal lesions are known. These include anti-rheumatics (steroid and non-steriod anti-inflammatory agents) such as corticosteroids (for example cortisone), salicylic acid derivatives (for example acetylsalicylic acid, diflunisal) or phenylalkanoic acids (for example piroxicam, acemetacin, pimetacin, nambumetone, carprofen, priprofen, fenclofenac, sulindac, indometacin, fenoprofen, tiaprofenic acid, tolmetin, flurbiprofen, suprofen, indoprofen, ibuprofen, naproxen, alclofenac, ketoprofen, diclofenac) or pyrazolones (phenylbutazone, metamizole), and also hypotensive agents (for example reserpine), vasodilators based on xanthine (for example pentoxyfylline), tuberculostatic agents (for example rifampicin) or cytostatics (for example methohexate).

The formulations according to the invention, used medically as pharmaceutical products, can contain the conventional pharmaceutical auxiliaries and excipients, which are suitable for the preparation of orally and dermally (and also, for example, nasally, sublingually, rectally and intravaginally) active medicaments. These include, for example, starch, sucrose, calcium sulfate, gelatine, starch paste, syrup, wheat starch and corn starch, stearic acid, stearate salts, sugars, saccharin, food constituents for animals, such as fats, carbohydrates, proteins and mineral solids; preservatives, sweeteners, dyestuffs, spices or suspending agents, mineral and vegetable oils such as peanut oil, olive oil, evening primrose oil, soya oil, sunflower oil, cotton seed oil, fish oil and sesame oil or fractions of these oils, both ionic and non-ionic detergents (for example as described below), preservatives and fungicides such as parabens, chlorobutanol, benzyl alcohol, phenol and thimerosal, and isotonic agents such as sugar or sodium chloride. The polyunsaturated fatty acids can also be absorbed on or mixed with polydextran or gels of polyacrylamide, alkylsulfate or alkylphosphate, or on aluminum hydroxide or silica.

The preparations for dermal administration are, for example, aqueous, alcoholic or polyol-containing solutions or suspensions, oily solutions or suspensions, or powders for subsequent incorporation into a dermally applicable form by addition of the requisite carrier. The solutions or suspensions are formulated with the requisite pharmaceutical auxiliaries and excipients containing, for example, fats, waxes, petroleum jelly or paraffin, and preservatives, suspending and dispersing agents and isotonic agents, such as, for example, methylparaben and propylparaben, sodium chloride, polyethylene glycols, especially polyethylene glycol 4000, sodium carboxymethyl cellulose, sodium alginate, polyvinylpyrrolidon, sorbimacrogol oleate, a condensation product of ethylene oxide with fatty acids, for example polyoxyethylene stearate, or with fatty alcohols such as, for example, heptadecaethylenoxycetanol, or with partial esters such as, for example, polyoxyethylene-sorbitol monooleate, or hexitans originating from sorbitol, such as, for example, polyoxyethylene-sorbitan monooleate. Suspensions in oily media are prepared by dispersing the active compound in the abovementioned oils. These suspensions can contain agents which delay absorption, such as, for example, aluminum monostearate. A dry product, for example a freeze-dried product, which can be mixed with a suitable pharmaceutical carrier at the desired time, represents a further embodiment. Preparations from the active compound, such as, for example, tablets, capsules, suppositories, syrups, solutions, suspensions and elixirs, contain pharmaceutical auxiliaries which render the preparation suitable for these administration forms in order to achieve the medical effect. The mixtures according to the invention are mixed with pharmaceutical auxiliaries such as lactose, starch, acacia gum, gelatin, talc and the like and processed to give capsules, tablets and the like or to give conventional suppository compositions, for example those based on triglycerides, such as, for example witepsol suppository compositions (H. P. Fiedler, Lexikon der Hilfsstoffe für Pharmazie, Kosmetik und angrenzende Gebiete [Dictionary of Auxiliaries for Pharmacy, Cosmetics and Related Fields], 1971, volume 9, pages 548–50 and 632–634, or for intravaginal suppositories U.S. Pat. Nos. 263,026 and 663,145); if appropriate, fatty alcohols; solid hydrocarbons, such as petroleum jelly or paraffin solidum; saturated fatty acids, such as lauric acid, myristic acid, palmitic acid and stearic acid; emulsifiers such as ethoxylated triglycerides and polyethoxylated vegetable oils; fatty acid sugar esters; silicones; gelatin; methyl cellulose; hydroxypropoxy cellulose and hydroxypropyl cellulose; polyethylene glycols; polyvinylpyrrolidone; polyvinyl alcohol; polyacrylic acid and salts thereof, or are mixed with water, suspending agents, sucrose, preservatives or hydro-alcoholic excipients and processed to give suspensions solutions or elixirs. It may be desirable for the unsaturated fatty acid to be released slowly or with delay from the pharmaceutical formulation. Such a delayed release can be accomplished in accordance with the state of the art. It depends on the pH of the biological medium whether the delayed release is accomplished, for example, by means of polystyrene or polyacrylic derivatives (Eudragit(®)) or, for example, by binding to a suitable ion exchanger. Enterically coated products, for example tablets, capsules, pills, beads or microbeads, can also be prepared. They are in the form of dosage units, for example as a single tablet or capsule or in the form of a collection of pills, microbeads or microspheres which have enteric properties and a prolonged action. Such enterically coated products and the coating materials used for this purpose are described in the literature, for example in U.S. Pat. Nos. 2,093,462 and 2,196,768 (cellulose acetate phthalate), 2,897,121 (copolymers of styrene and maleic acid), 3,081,233 and others.

EXPERIMENTAL PART

Method 1: Investigation of the Stability of Unsaturated Fatty Acids in the Formulations The stabilizing action of substances on polyunsaturated fatty acids was investigated as follows:

Test A for Water-Soluble Substances:

0.125 mg of unsaturated fatty acid or Na salt (see tables) (sodium arachidonate, from Sigma, Munich, Germany) is dissolved in 0.05 ml of water. 0.2 ml of aqueous solution which contains 2 mg of stabilizer and can additionally contain 2 mg of stimulator is mixed in (cf. Table 1), 0.1 ml is then taken out immediately, extracted and analysed (see below). Further processing according to modification 1 or 2.

Modification 1 for Aqueous Solutions

After 24 hours incubation at 37° C., 0.1 ml is again taken, extracted and analysed (see below).

Modification 2 for Solid Mixtures (Lyophilisates)

The test solution is lyophilized, the lyophilisate is incubated for 24 hours at 37° C. and then dissolved again in the previous quantity of water, and 0.1 ml is taken, extracted and analysed (see below).

Test B for Water-Insoluble Substances:

0.125 mg of unsaturated fatty acid (arachidonic acid, 5,8,11,14,17-eicosapentaenoic acid or 8,11,14-eicosatrienoic acid, from Sigma, Munich) is dissolved in 0.05 ml of ethanol or dimethyl sulfoxide. 0.2 ml of ethanol (or dimethyl sulfoxide) which contains 2 mg of stabilizer and can additionally contain 2 mg of the stimulator (cf. Table 1) is added thereto, and 0.1 ml is taken immediately and, as below, extracted and analysed. Further treatment according to modification 1 or 2.

Modification 1 for Solutions

After 24 hours' incubation at 37° C., 0.1 ml is again taken, mixed with 0.1 ml of water, extracted and analysed.

Modification 2 for Solid Mixtures

The remaining solution is freed of solvent, incubated for 24 hours at 37° C. and then dissolved again in 0.15 ml of solvent, and 0.1 ml is taken, mixed with 0.1 ml of water, extracted and analysed.

Extraction and Analysis 0.05 ml of 1.2M aqueous citric acid solution is added to the samples obtained, and the samples are extracted with twice 0.5 ml of ethyl acetate, the ethyl acetate is removed from the combined extracts and the residue is dissolved in 0.8 ml of methanol and analysed by means of high-pressure liquid chromatography (HPLC) (Rad Pak C-18 column, 100×8 mm, from Waters, Königstein, Germany, 1.5 ml/minute, solvent 800 ml of methanol, 200 ml of water and 0.1 ml of glacial acetic acid). The separation is monitored with a commercially available UV detector at 206 nm.

Method 2: Prostaglandin Synthesis 0.3 ml of 0.03M potassium phosphate buffer of pH=8.0 contains 0.5 mg of enzyme (from seminal vesicles of sheep) (Biochemistry 10 (1971) 2372) or homogenate of the inner kidney medulla (Life Sciences 26 (1980) 765), 2.75 μg of $^{14}C$-arachidonic acid (0.5 μCi) and 0.5 mg of stimulator and, if appropriate, 0.5 mg of stabilizer substance (see Table 1). After 10 minutes' incubation at 37° C., the reaction is stopped with 0.05 ml of 1.2M citric acid and the mixture is extracted with twice 0.5 ml of ethyl acetate, the combined extracts are freed of solvent, and the residue is dissolved in 0.2 ml of methanol, diluted 1:1 with water and separated by HPLC (nucleosil C-18 column, 125×4.6 mm, from Bischoff, Leonberg, Germany, solvent 300 ml of acetonitrile, 700 ml of water and 1 ml of glacial acetic acid and after 30 minutes pure methanol). The separation of the radioactive fractions is followed by a monitor (LB 504 from Berthold, Wildbad, Germany). The products formed, such as 6-keto-prostaglandin $F_{2alpha}$, prostaglandin $E_2$, prostaglandin $F_{2alpha}$ and prostaglandin $D_2$, are separated under these conditions.

TABLE 1 STIMULATION OF THE PROSTAGLANDIN FORMATION IN STABILIZED FATTY ACID FORMULATIONS

The prostaglandins $PGE_2$, $PGF_2alpha$ and $PGD_2$ as products from arachidonic acid where quantified by means of method 2, and the sum was related as "total prostaglandin" to 100%. The quantity of "total prostaglandin" formed without the addition of a stimulator was set at f=1; the quantity formed after stimulation was related thereto. f=2 or f=3 therefore means twice or three times the stimulation under the conditions of method 2. The stability of the sample was investigated by means of method 1 (right-hand column). Without additions (right-hand column: A), 25–28% of the arachidonic acid remain in aqueous solution under these conditions. Values greater than 25–28% therefore represent a stabilization, and values smaller than 25–28% represent a destabilization. Example No. 1 was carried out without a stimulator. The effects according to the invention can be obtained with the stabilized formulations from the correspondingly designated examples. The substances test with respect to stabilization (see Method 1 for quantities) were: A) aqueous solution without stabilizer addition, B) ethanolic solution without further addition, C) pyridine solution, D) with rutin, predissolved in dimethyl sulfoxide, dimethyl sulfoxide then stripped off, E) like B) with lecithin, ethanol stripped off, F) like A) with cytochrome c from horse heart (from Boehringer, Mannheim, Germany), G) like A) with methemoglobin (human) (from Sigman, Munich, Germany), H) like A) with bovine serum albumin (from Calbiochem, Frankfurt, Germany), J) like A) or B), but solvent stripped off, K) like J) with cytochrome c, L) like J) with hemoglobin (human) (from Behringwerke, Marburg, Germany), and M) like J) with human serum albumin (from Behringwerke, Marburg, Germany).

| Example No. | Stimulator | Arachidonic acid product (Method 2) relative total prostaglandin f | PGE₂ % | PGF₂ₐₗₚₕₐ % | PGD₂ % | Stability (% of remaining arachidonic acid by Method 1) | | | |
|---|---|---|---|---|---|---|---|---|---|
| | | Comparative investigation | | | | | | | |
| (1) | without stimulator | 1 | 83 | 2 | 15 | A | 26 | G | 90 |
| | | | | | | B | 100 | H | 100 |
| | | | | | | C | 13 | J | 0 |
| | | | | | | D | 97 | K | 100 |
| | | | | | | E | 90 | L | 85 |
| | | | | | | F | 98 | M | 100 |
| | | Examples of substances not according to the invention | | | | | | | |
| (2) | m-cresol | 0.61 | 98 | 0 | 2 | | | | |
| (3) | phenol | 0.95 | 77 | 5 | 18 | | | | |
| (4) | L-phenylalanine | 0.9 | 80 | 2 | 18 | | | | |
| (5) | trans-cinnamic acid | 0.9 | | | | | | | |
| | Examples of compounds according to the invention of the formula I | | | | | | | | |
| (6) | $R_1 = -CH_2-CH(CO_2H)-NH_2$; $R_2 = R_3 = -H$ | 5,5 | 81 | 2 | 17 | A | 91 | J | 98 |
| | | | | | | B | 100 | K | 100 |
| | | | | | | C | 67 | M | 100 |
| (7) | $R_1 = -CH_2-CH_2-NH_2$; $R_2 = R_3 = -H$ | 4,0 | 80 | 3 | 17 | A | 87 | | |
| (8) | $R_1 = -CH_2-CH_2-CO_2H$; $R_2 = R_3 = -H$ | 4,5 | 83 | 1 | 16 | A | 89 | | |
| (9) | $R_1 = -CH_2-CH(CO_2H)-NH_2$; $R_2 = -OH$; $R_3 = -H$ | 9.4 | 70 | 14 | 16 | A | 15 | F | 97 |
| | | | | | | B | 97 | G | 96 |
| | | | | | | C | 93 | M | 100 |
| (10) | $R_1 = -CH_2-CH_2-NH_2$; $R_2 = -OH$; $R_3 = -H$ | 6.0 | 52 | 35 | 13 | A | 17 | H | 100 |
| | | | | | | B | 95 | K | 98 |
| | | | | | | C | 9 | M | 100 |
| (11) | $R_1 = -CH_2-CH(CONH_2)-NH-C(=O)-CH_3$ | (Stimulation: positive) | | | | A | (Stabilization: positive) | | |
| (12) | $R_1 = -CHOH-CH_2-NH_2$; $R_2 = -OH$; $R_3 = -H$ | 8.3 | 66 | 17 | 17 | A | 11 | F | 99 |
| | | | | | | B | 93 | G | 95 |
| | | | | | | D | 93 | M | 100 |
| (13) | $R_1 = -CHOH-CH_2-NHCH_3$; $R_2 = -OH$; $R_3 = -H$ | 13 | 70 | 12 | 18 | A | 9 | H | 97 |
| | | | | | | B | 92 | J | 0 |
| | | | | | | E | 94 | M | 100 |
| (14) | $R_1 = -OH$; $R_2 = R_3 = -H$ | 3,2 | 69 | 12 | 19 | A | 7 | G | 99 |
| | | | | | | D | 97 | K | 97 |
| | | | | | | F | 98 | M | 99 |
| (15) | $R_1 = -CO_2H$; $R_2 = -OCH_3$; $R_3 = -H$ | 5.1 | 71 | 12 | 17 | A | 22 | F | 98 |
| | | | | | | B | 100 | G | 96 |
| | | | | | | D | 98 | J | 17 |
| (16) | $R_1 = -CO_2H$; $R_2 = R_3 = -H$ | 4.5 | 69 | 13 | 18 | A | 21 | F | 98 |
| | | | | | | B | 98 | G | 96 |
| | | | | | | D | 97 | H | 99 |
| (17) | $R_1 = -CH=CHCO_2H$; $R_2 = -OH$; $R_3 = -H$ | 5.7 | 70 | 13 | 17 | A | 19 | H | 99 |
| | | | | | | D | 99 | J | 16 |
| | | | | | | G | 95 | M | 98 |
| | Examples of compounds of the formula II, according to the invention | | | | | | | | |
| (18) | $R_1 = -CO_2H$; $R_2 = -NH_2$; $R_3 = -H$ | 9.8 | 76 | 3 | 21 | A | 18 | H | 98 |
| | | | | | | D | 99 | J | 15 |
| | | | | | | G | 99 | K | 99⁽¹⁾ |
| (19) | $R_1 = -CO_2H$; $R_2 = -NH_2$; $R_3 = -OH$ | 10.1 | 79 | 3 | 18 | A | 17 | E | 95 |
| | | | | | | B | 95 | F | 97 |
| | | | | | | D | 96 | G | 95 |
| (20) | $R_1 = -CO_2H$; $R_2 = R_3 = -H$ | 5.1 | 82 | 2 | 16 | A | 20 | F | 98 |
| | | | | | | B | 100 | H | 99 |
| | | | | | | E | 96 | M | 99 |
| (21) | $R_1 = -CO_2H$; $R_2 = -H$; $R_3 = -OH$ | 5.7 | 80 | 3 | 17 | A | 18 | G | 96⁽²⁾ |
| | | | | | | B | 99 | H | 97 |
| | | | | | | F | 98 | J | 12 |
| (22) | $R_1 = -H$; $R_2 = -NH_2$ | 10.6 | 75 | 5 | 20 | A | 16 | F | 98 |
| | | | | | | B | 99 | K | 98 |

-continued

| Example No. | Stimulator | Arachidonic acid product (Method 2) | | | | Stability (% of remaining arachidonic acid by Method 1) | | | |
|---|---|---|---|---|---|---|---|---|---|
| | | relative total prostaglandin f | PGE$_2$ % | PGF$_{2alpha}$ % | PGD$_2$ % | | | | |
| (23) | R$_3$ = —OH<br>R$_1$ = —H<br>R$_2$ = —NH$_2$<br>R$_3$ = —H | 6.1 | 81 | 3 | 16 | E<br>A<br>D<br>E | 96<br>20<br>100<br>97$^{(1)}$ | L<br>F<br>G<br>H | 100<br>98<br>97<br>100 |

Examples of peptides according to the invention, containing tyrosine (Tyr) or tryptophan (Trp)

| Example No. | Stimulator | rel. tot. prosta. f | PGE$_2$ % | PGF$_{2alpha}$ % | PGD$_2$ % | | | | |
|---|---|---|---|---|---|---|---|---|---|
| (24) | Trp—Trp | 11.7 | 75 | 2 | 23 | A<br>B<br>C | 17<br>98<br>12 | D<br>F<br>G | 97<br>97<br>96 |
| (25) | Gly—Trp—Gly | 13.0 | 79 | 1 | 20 | A<br>F<br>G | 18<br>96<br>97 | H<br>J<br>K | 99<br>7<br>99 |
| (26) | Trp—Ala | 12.6 | 77 | 1 | 22 | A<br>D | 19<br>98 | E<br>F | 92<br>96 |
| (27) | Leu—Trp | 17.0 | 77 | 1 | 22 | A<br>B | 20<br>99 | F<br>M | 98<br>100 |
| (28) | Trp—Met—Asp—Phe | 11.8 | 73 | 7 | 20 | A<br>D | 17<br>97 | D<br>F | 97$^{(1)}$<br>96 |
| (29) | Leu—Trp—Met | 10.8 | 69 | 9 | 22 | A<br>B<br>D | 18<br>99<br>97 | H<br>J<br>K | 99<br>7<br>100 |
| (30) | Tyr—Tyr—Tyr—OCH$_3$ | 5.3 | 75 | 4 | 11 | A<br>B | 94<br>98 | J<br>K | 98<br>100 |
| (31) | Tyr—Trp | 6.3 | 73 | 3 | 14 | A<br>B | 80<br>97 | D<br>M | 98<br>100 |
| (32) | Cyclo-Trp—Tyr | (Stimulation: positive) | | | | (Stabilization: positive) | | | |

Examples of sulfur-containing compounds according to the invention

| (33) | L-cysteine | 4.0 | 56 | 17 | 27 | A<br>B<br>D | 9<br>95<br>94$^{(3)}$ | D<br>H<br>M | 95<br>96<br>96 |
|---|---|---|---|---|---|---|---|---|---|
| (34) | D-cysteine | 3.5 | 63 | 14 | 23 | A<br>D<br>D | 13<br>96<br>95 | H<br>J<br>K | 97<br>5$^{(2)}$<br>98 |
| (35) | Glutathione | 13.5 | 100 | 0 | 0 | A<br>B<br>C | 0<br>80<br>0 | H<br>J<br>L | 91<br>0<br>92 |
| (36) | Lipoic acid | 5.5 | 43 | 49 | 8 | A<br>E<br>F | 92<br>94<br>100 | G<br>J<br>L | 100<br>90<br>100 |
| (37) | N—Acetylcysteine | 4.0 | 61 | 14 | 25 | A<br>B<br>D | 9<br>93<br>95 | E<br>F<br>G | 93<br>98<br>98 |
| (38) | Tyr—Cys—Glu—His—<br>—Phe—Arg—Trp—Gly | (Stimulation: positive) | | | | M | 100 | | |

Sulfur-containing compounds not according to the invention

| (39) | Dithiothreitol | 0.8 | | | | | | | |
|---|---|---|---|---|---|---|---|---|---|
| (40) | Dithioerythritol | 0.85 | | | | | | | |
| (41) | Cystine | 1.0 | 85 | 0 | 15 | | | | |
| (42) | Dihydrolipoic acid | 1.0 | | | | | | | |
| (43) | Cysteamine | 0.9 | | | | | | | |
| (44) | Mercaptoethanol | 0.95 | | | | | | | |
| (45) | Coenzyme A | 1.0 | | | | | | | |
| (46) | Pantetheine | 0.95 | | | | | | | |

$^{(1)-(3)}$instead or arachidonic acid, 5,8,11,14,17-eicosapentaenoic acid was used in $^{(1)}$, 8,11,14-eicosatrienoic acid was used in $^{(2)}$, and 9,12,15-linolenic acid was used in $^{(3)}$.
$^{(4)}$Hare gamma-globulin (from Calbiochem, Frankfurt)

TABLE 2

Investigations of the properties, according to the invention, of vitamins, flavonoids, cyclodextrins and (sugar-) lipid compounds. The fatty acids used in the stabilization experiment are indicated in brackets. (A = arachidonic acid, E = 5,8,11,14,17-eicosapentaenoic acid)

| Example No. | Stimulator | Arachidonic acid product (Method 2) | | | | Stabilization (% remaining unsaturated fatty acid by Method 1) |
|---|---|---|---|---|---|---|
| | | relative total prostaglandin f | PGE$_2$ % | PGF$_{2alpha}$ % | PGD$_2$ % | |
| Vitamins not according to the invention | | | | | | |
| (47) | Vitamin Q$_{10}$ | 0.8 | 8 | 78 | 14 | 8% (A) |

-continued

| Example No. | Stimulator | Arachidonic acid product (Method 2) relative total prosta- glandin f | PGE$_2$ % | PGF$_{2alpha}$ % | PGD$_2$ % | Stabilization (% remaining unsaturated fatty acid by Method 1) |
|---|---|---|---|---|---|---|
| (48) | Vitamin B$_{12}$ | | | | | 6% (A) |
| (49) | Vitamin C | | | | | 0% (A) |
| | Vitamins according to the invention | | | | | |
| (50) | DL-alpha-Tocopherol | | | | | 78% (A) |
| (51) | D-alpha-Tocopheryl- quinone | 0.5 | 80 | 5 | 15 | 98% (A) |
| | Sugar-containing flavonoids according to the invention | | | | | |
| (52) | Rutin | 6 | 76 | 6 | 18 | 97% (A) 96% (E) |
| (53) | Phlorizin | 3 | 80 | 2 | 18 | 97% (E) |
| (54) | Naringin | 2 | 83 | 2 | 15 | 96% (A) |
| | Flavonoids according to the invention without a sugar moiety | | | | | |
| (55) | Naringenin | 1.5 | 80 | 0 | 20 | 96% (A) |
| (56) | Kaempferol | 0.5 | 76 | 11 | 13 | 98% (E) |
| (57) | Quercetin | 0.3 | 72 | 18 | 10 | 92% (E) |
| (58) | Catechin | 0.2 | 70 | 18 | 12 | 90% (A) |
| (59) | Epicatechin | 0.15 | 71 | 17 | 12 | 89% (A) |
| (60) | Phloretin | 0.15 | 76 | 11 | 13 | 97% (A) |
| (61) | Morin | 0.08 | 54 | 27 | 19 | 100% (E) |

All the flavonoids investigated stabilize the polyunsaturated fatty acids. The sugar-containing flavonoids are particularly suitable according to the invention, because they stimulate the formation of the prostaglandins. Particularly for the use according to the invention in vitro, the flavonoids without a sugar moiety are less suitable, because they inhibit the prostaglandin synthesis.

| | Cyclodextrins according to the invention | |
|---|---|---|
| (62) | alpha-Dextrin (Cyclohexaamylose) | 60% (A) |
| (63) | beta-Dextrin (Cycloheptaamylose) | 90% (A) 88% (E) |
| (64) | gamma-Dextrin (Cyclooctaamylose) | 75% (A) |
| | Lipids according to the invention (from Serva, Heidelberg) | |
| (65) | Sucrose palmitate stearate 7 SPS-7 | 91% (A) 92% (E) |
| (66) | Sucrose palmitate stearate 15 SPS-15 | 92% (A) |
| (67) | Na dioctylsulfosuccinate | 94% (A) |

EXAMPLES OF STABLE FORMULATIONS ACCORDING TO THE INVENTION, INCLUDING PHARMACEUTICAL FORMULATIONS

Examples 68 to 70

50 mg of sodium arachidonate, 500 mg of bovine serum albumin and 500 mg of L-tyrosine are dissolved under sterile conditions in 10 ml of twice distilled water and, likewise under sterile conditions, stored in a brown bottle. 93.5% of the arachidonic acid originally present are recovered after 6 weeks' storage at room temperature, whereas the same sodium arachidonate solution without additions virtually no longer contain any arachidonic acid after this time (content <0.8). The stabilized solution prepared in this way Example 68 filled into a drinking ampoule for medical purposes, Example 69 treated with 15 mg of seminal vesicles of sheep and incubated for 60 minutes at 37° C., and the prostaglandins formed are then extracted and preparatively isolated as described in Method 2, or or Example 70 used for the clinical-biochemical determination of the thrombophilia of test subjects (patients), by adding 1 ml of lyzed platelet-rich blood plasma from these test subjects to 0.01 ml of this stabilized sodium arachidonate solution and extracting after 30 minutes' incubation at 25° C. The prostaglandin D$_2$ formed (Method 2) is used as a measure of the thrombophilia of the patient.

Example 71

100 mg of 5,8,11,14,17-eicosapentaenoic acid and 500 mg of rutin are taken up together in 15 ml of dimethyl sulfoxide, the dimethyl sulfoxide is completely stripped off and the residue is transferred, together with acetyl salicylic acid crystals (500 mg of R 95 D, from Röhm Pharma, Darmstadt, Federal Republic of Germany) into size O gelatin capsules (from Kapsugel, Basel, Switzerland).

Example 72

1 g of L-alpha-lecithin, beta, gamma-dipalmitoyl (from Calbiochem GmbH, Frankfurt/Main, Germany), 100 mg of arachidonic acid, 100 mg of lipoic acid and 100 mg of DL-alpha-tocopherol acetate (from Aldrich, Steinheim, Germany) are stirred into 10 ml of twice distilled water, and the mixture is homogenized by ultrasonic treatment.

Example 73

170 mg of wheat starch, 450 mg of lactose, 20 mg of magnesium stearate, 5 mg of sodium arachidonate, 10 mg of tryptophan and 20 mg of troxerutin (from Aldrich, Steinheim, Germany) are ground, intimately mixed and pressed to give a tablet.

Example 74

150 mg of wheat starch, 435 mg of lactose, 15 mg of magnesium stearate, 5 mg of sodium arachidonate and 15 mg of lipoic acid are intimately mixed by grinding and pressed to give a tablet.

Example 75

10 mg of sodium arachidonate are taken up with 20 mg of serotonine and 100 mg of hemoglobin (reduced, from Calbiochem GmbH, Frankfurt) in 3.5 ml of water (twice distilled) and lyophilized. The residue can be processed to give dosage units in capsules (size O gelatin capsules from Kapsugel, Basel, Switzerland).

Example 76

15 mg of 8,11,14-eicosatrienoic acid are taken up with 50 mg of N-acetylcysteine and 100 mg of cytochrome c from horse heart (from Aldrich, Steinheim, Germany) in 2 ml of water (twice distilled).

Example 77

40 mg of arachidonic acid are taken up under sterile conditions with 180 mg of beta-cyclodextrin and 60 mg of 5-hydroxytryptamin in 50 ml of water (twice distilled).

Example 78 a–f

6 Batches a, b, c, d, e and f are prepared which each contain, in 1 ml of ethanol, 0.7 mg of arachidonic acid and, respectively, a) 1, b) 5, c) 10, d) 25, e) 50 and f) 100 mg of lipoic acid. After the ethanol has been stripped off, these batches can be kept for at least 12 days at 37° C. The determination according to Method 2 gave still 99±2% of arachidonic acid in the batches after 12 days.

Examples 79–82

0.125 mg of arachidonic acid are taken up in 0.25 ml of water, which contains 5 or 25 or 50 or 75 percent by weight of dimethyl sulfoxide, and the mixtures are incubated at 37° C. Extraction and analysis are carried out after 24 hours. A typical analysis gave

|  | % of dimethyl sulfoxide | % of arachidonic acid |
| --- | --- | --- |
| Example (79) | 5 | 54 |
| Example (80) | 25 | 75 |
| Example (81) | 50 | 83 |
| Example (82) | 75 | 94 |

Example 83

2 g of arachidonic acid and 1 g of tyrosamine are stirred into 5 ml of glycerole triacetate and uniformly distributed by ultrasonic treatment at 30° C.

I claim:

1. A formulation for the synthesis of prostaglandins and hydroxy-fatty acids in biological systems, which comprises:
   at least one unsaturated fatty acid, defined by three to five isolated double bonds at 18 to 22 carbon atoms which are arranged in a straight chain and can be methylated or ethylated at one or two carbon atoms in positions 2, 3, 4, 16, 17, 18, 19 or 20, as the free carboxylic acid with terminal —CO$_2$H, or as the carboxamide or as —CO$_2$X, X being a protective group which can be eliminated under acidic conditions or a 1- or 2-lysophospholipid or a metal or amine cation or the cationic form of an ion exchanger, and
   a stimulator capable of exhibiting a simultaneous stabilizing action selected from a cysteine, a homocysteine or a lipoic acid, the acyclic alkyl radical of which can be shortened up by to four methylene groups, with a stabilizer selected from phospholipids, sugar lipids, cyclodextrins, proteins, cytochromes of the C series or vitamins of the E series, in the solid or liquid form,
   wherein the weight ratio of the unsaturated fatty acid to the stimulator is between 50 and 0.1, and the weight ratio of the free unsaturated fatty acid to the stabilizer is between about 100 and 0.5.

2. A formulation as claimed in claim 1, wherein the fatty acids include 18:2 ω-6, 20:4 ω-6, 22:5 ω-6, 18:3 ω-3, 20:5 ω-3, 22:6 ω-3, 18:3 ω-6, 20:3 ω-6, 22:4 ω-6 or 22:4 ω-3 fatty acids and the stimulator is lipoic acid, the side chain of which can be shortened by up to four CH$_2$ groups.

3. A formulation as claimed in claim 1, wherein the stabilizer is betadextrin, lecithin, proteins which can be prepared from human or mammal blood, or cytochromes of the C series.

4. A formulation as claimed in claim 1, wherein the stabilizer is hemoglobin or methemoglobin, globulin or serum albumin.

5. A formulation as claimed in claim 1, wherein the fatty acid is arachidonic acid, 5,8,11,14,17-eicosapentaenoic acid, 8,11,14-eicosatrienoic acid or 9,12,15-linolenic acid.

6. A formulation as claimed in claim 1, wherein the weight ratio is between about 20 and 0.5.

7. A formulation as claimed in claim 1, wherein the weight ratio is between about 15 and 1.

8. A formulation as claimed in claim 1, which is in a form to be administered dermally, orally, perorally or as suppositories.

9. A formulation as claimed in claim 1, which contains, per dosage unit, from about 0.5 to 2,000 mg of unsaturated fatty acid.

10. A formulation as claimed in claim 9, which contains from about 5 to 250 mg of unsaturated fatty acid.

11. A formulation as claimed in claim 1, wherein the unsaturated fatty acids are at least partially in a retarded form.

12. A formulation for the synthesis of prostaglandins and hydroxy-fatty acids in biological systems, which comprises at least one unsaturated fatty acid and at least one stimulator selected from a cysteine, a homocysteine or a lipoic acid, with at least one stabilizer;
   wherein the weight ratio of the unsaturated fatty acid to the stimulator is between 50 and 0.1, and the weight ratio of the free unsaturated fatty acid to the stabilizer is between about 100 and 0.5.

13. A formulation as claimed in claim 11, which contains, per dosage unit, between 0.5 and 2,000 mg of unsaturated fatty acid.

14. A formulation as claimed in claim 13, which contains from about 5 to 250 mg of unsaturated fatty acid.

15. A method of treating a patient suffering from prostaglandin deficiencies which comprises administering to the patient in need of such a treatment a formulation as claimed in claim 10.

16. A method of treating a patient suffering from diseases of the gastro-intestinal tract which comprises administering to the patient in need of such a treatment a formulation as claimed in claim 1.

* * * * *

UNITED STATES PATENT AND TRADEMARK OFFICE
CERTIFICATE OF CORRECTION

PATENT NO. : 5,043,328
DATED : August 27, 1991
INVENTOR(S) : Klaus-Ulrich Weithmann It is certified that error appears in the above-identified patent and that said Letters Patent is hereby corrected as shown below:

Claim 1, column 18, line 4, change "up by to"
to --by up to--.

Signed and Sealed this

Thirtieth Day of March, 1993

Attest:

STEPHEN G. KUNIN

*Attesting Officer*    Acting Commissioner of Patents and Trademarks